US012496389B2

(12) United States Patent
Zhu et al.

(10) Patent No.: US 12,496,389 B2
(45) Date of Patent: Dec. 16, 2025

(54) INTRAOSSEOUS PRESSURE RELEASE SCREW

(71) Applicant: SICHUAN UNIVERSITY, Chengdu (CN)

(72) Inventors: Songsong Zhu, Chengdu (CN); Shan Chen, Chengdu (CN)

(73) Assignee: Sichuan University, Sichuan (CN)

( * ) Notice: Subject to any disclaimer, the term of this patent is extended or adjusted under 35 U.S.C. 154(b) by 1392 days.

(21) Appl. No.: 16/465,395

(22) PCT Filed: Feb. 1, 2018

(86) PCT No.: PCT/CN2018/074898
§ 371 (c)(1),
(2) Date: Aug. 24, 2021

(87) PCT Pub. No.: WO2018/166303
PCT Pub. Date: Sep. 20, 2018

(65) Prior Publication Data

US 2022/0088291 A1 Mar. 24, 2022

(30) Foreign Application Priority Data

Mar. 15, 2017 (CN) ......................... 201710153443.8

(51) Int. Cl.
*A61M 1/00* (2006.01)
*A61M 3/02* (2006.01)

(52) U.S. Cl.
CPC ................ *A61M 1/71* (2021.05); *A61M 1/84* (2021.05); *A61M 3/0279* (2013.01); *A61M 2205/7545* (2013.01); *A61M 2210/02* (2013.01)

(58) Field of Classification Search
CPC ........ A61M 1/71; A61M 1/84; A61M 3/0279; A61M 2205/7545; A61M 2210/02; Y02A 50/30; A61B 17/864
See application file for complete search history.

(56) References Cited

U.S. PATENT DOCUMENTS 5,273,545 A * 12/1993 Hunt .................. A61B 17/3498 604/167.04
5,746,720 A * 5/1998 Stouder, Jr. ........ A61B 17/3417 604/23

(Continued)

FOREIGN PATENT DOCUMENTS

CN 201939750 U 8/2011
CN 201996885 U 10/2011

(Continued)

OTHER PUBLICATIONS

International Search Report Dated Apr. 27, 2018.

*Primary Examiner* — Rebecca E Eisenberg
*Assistant Examiner* — Matthew Wrubleski
(74) *Attorney, Agent, or Firm* — Caesar Rivise, PC

(57) ABSTRACT

The invention is related to the field of medical device, particularly to an intraosseous pressure release screw which not only excludes foreign matters but also facilitates intraosseous cleaning. The intraosseous pressure release screw comprises a screw rod with a central cavity disposed therein and a screw cap rotatably disposed on one end of the screw rod; the screw cap is provided with a pressure release part which communicates the central cavity with the outside; a rinsing opening is arranged on the rod section of the screw rod within the screw cap and is in communication with the central cavity; and a lockable opening is arranged on the side wall of the screw cap and can rotate with the screw cap to keep communication with the rinsing opening. As a screw cap with a pressure release part is arranged at the end of the (Continued)

screw rod, the food blockage of the screw rod can be prevented while the patient under treatment is eating, thereby ensuring the unobstructed pressure release. In the case of intraosseous cleaning, the screw cap is rotated to a position where the lockable opening is in communication with the rinsing opening; that is, the rinsing solution may be added to the central cavity via the rinsing opening, thus improving the therapeutic effect of core decompression.

17 Claims, 9 Drawing Sheets

(56) References Cited

U.S. PATENT DOCUMENTS

2007/0065782 A1 3/2007 Maschke
2012/0109111 A1 5/2012 Li
2013/0072847 A1* 3/2013 Schutz .............. A61M 39/0247
604/6.16
2016/0081732 A1* 3/2016 Baroud ............ A61B 5/150389
623/23.62
2018/0092632 A1* 4/2018 Rioux ................ A61B 17/3472

FOREIGN PATENT DOCUMENTS

CN 202236874 U 5/2012
CN 106730072 A 5/2017
WO WO-0112086 A1 * 2/2001 ......... A61B 17/3415

* cited by examiner

INTRAOSSEOUS PRESSURE RELEASE SCREW

CROSS-REFERENCE TO RELATED APPLICATIONS

This application is a U.S. National Phase Application of PCT/CN2018/074898, filed Feb. 1, 2018, which claims priority to 201610598677.9, filed Jul. 27, 2016, the contents of which applications are incorporated herein by reference in their entireties for all purposes.

TECHNICAL FIELD

The invention is related to the field of medical device, in particular to an intraosseous pressure release screw.

BACKGROUND

Jaw cyst refers to a liquid-containing cystic mass in jaw which may gradually grow up and cause swelling and destruction of the jaw. At present, intraosseous pressure is generally released through a root canal or a pressure release screw during treatment of jaw cyst. The existing pressure release screw comprises a screw rod, wherein both the two ends and the interior of the screw rod are of cavity, and the side wall of the screw rod is provided with a through hole in communication with the interior cavity of the screw rod. As the two ends of the screw rod are opened, the opening at the tail end of the screw rod is often blocked by food while the patient under treatment is eating, which is not conducive to releasing the intraosseous pressure but easy to cause infection, thus seriously affecting the therapeutic effect.

SUMMARY OF THE INVENTION

The technical problem to be solved by the invention is to provide an intraosseous pressure release screw which not only can exclude foreign matters but also facilitate intraosseous cleaning.

The technical scheme for solving the technical problem in the invention is as follows: an intraosseous pressure release screw comprises a screw rod with a central cavity disposed therein and a screw cap rotatably disposed on one end of the screw rod; the screw cap is provided with a pressure release part communicating the central cavity with the outside; a rinsing opening is arranged on the rod section of the screw rod within the screw cap and is in communication with the central cavity; a lockable opening is arranged on the side wall of the screw cap and can rotate with the screw cap to keep communication with the rinsing opening.

Furthermore, the pressure release part comprises pressure release holes arranged on the screw cap.

Furthermore, the pressure release holes are arranged on the top of the screw cap, the two ends of the pressure release hole are respectively located on the inner and outer surfaces of the top of the screw cap, and the pressure release part further comprises a filter layer arranged on the outer surface on the top of the screw cap.

Furthermore, the pressure release part is arranged on the top of the screw cap and comprises at least two concave arc-shaped flaps with upper ends fitted to each other.

Furthermore, the pressure release part is arranged on the top of the screw cap and has a spherical arc surface closed end comprising at least three convex arc-shaped flaps.

Furthermore, the pressure release part is arranged at the top of the screw cap, and comprises a valve cavity with a lower air inlet end and an upper air outlet end, a valve core and a spring sequentially arranged in the valve cavity along the air flow direction; and a spring slot is arranged at the top wall of the valve cavity, with one end of the spring pressing against the valve core, and the other end of the spring pressing against the spring slot.

Furthermore, the pressure release part is arranged on the top of the screw cap, and comprises a cavity with a lower air inlet and an upper air outlet, and an elastic valve plate arranged in the cavity and closing the lower air inlet. When the pressure in the central cavity is greater than the atmospheric pressure, the free end of the elastic valve plate can move towards the upper air outlet to open the lower air inlet.

Furthermore, a valve plate fixing column is arranged on the bottom wall of the cavity located at one side of the lower air inlet, one end of the elastic valve plate is fixedly arranged on the valve plate fixing column, and the other end is attached to the bottom wall of the cavity on the other side of the lower air inlet.

Furthermore, the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto. When the screw cap is rotated until the first rod head is embedded into the first clasp, the lockable opening is not communicated with the rinsing opening. When the screw cap is rotated until the second rod head is embedded into the second clasp, the lockable opening is communicated with the rinsing opening.

Furthermore, an annular convex structure is arranged on the external side wall of the screw rod disposed on the upper side of the first rod head and the second rod head, and a concave structure matching with the convex structure is arranged on the inner wall of the screw cap; and the convex structure is embedded into the concave structure so that the screw rod and the screw cap are connected together and can rotate relatively.

The beneficial effects of the invention are as follows: as a screw cap with a pressure release part is arranged at the end of the screw rod, the food blockage of the screw rod can be prevented when the patient under treatment is eating. Thus, smooth pressure release is ensured. Further, a rinsing opening and a lockable opening in communication with the rinsing opening are provided. In the case of intraosseous cleaning, the screw cap is rotated to a position in which the lockable opening is in communication with the rinsing opening; that is, the rinsing solution may be added to the central cavity via the rinsing opening, thus improving the therapeutic effect of core decompression.

Figure 1:
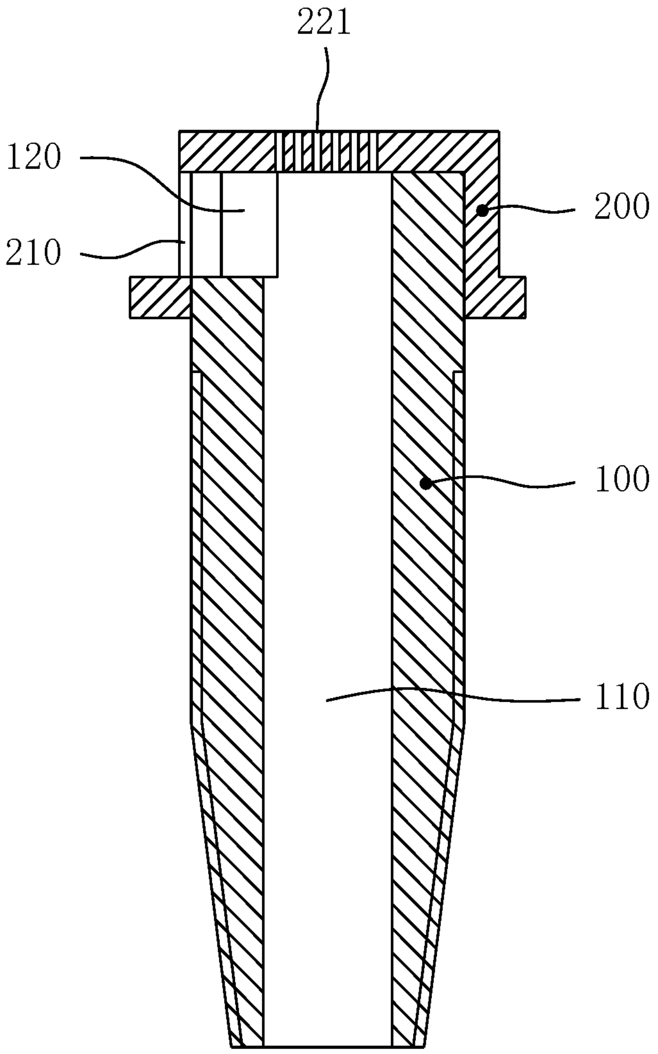
FIG. 1 is a schematic diagram of a first embodiment of the invention.

Designations in figures are follows: screw rod 100, central cavity 110, rinsing opening 120, first rod head 130, second rod head 140, convex structure 150, screw cap 200, lockable opening 210, pressure release hole 221, filter layer 222, concave arc-shaped flap 231, convex arc-shaped flap 241, valve cavity 251, lower air inlet end 252, upper air outlet end 253, valve core 254, spring 255, spring slot 256, O-shaped sealing ring 257, cavity 261, lower air inlet 262, upper air outlet 263, elastic valve plate 264, valve plate fixing column 265, first clasp 270, second clasp 280, concave structure 290, and protective guard 300.

DETAILED DESCRIPTION OF THE PREFERRED EMBODIMENTS

The invention will be further described in detail in combination with drawings.

As shown in FIG. 1, FIG. 3, FIG. 6, FIG. 7, FIG. 8, FIG. 9 and FIG. 10, an intraosseous pressure release screw comprises a screw rod 100 with a central cavity 110 disposed therein and a screw cap 200 rotatably disposed on one end of the screw rod 100; the screw cap 200 is provided with a pressure release part which communicates the central cavity 110 with the outside; and a rinsing opening 120 is arranged on the rod section of the screw rod 100 within the screw cap 200 and is in communication with the central cavity 110; a lockable opening 210 is arranged on the side wall of the screw cap 200 and can rotate with the screw cap 200 to keep communication with the rinsing opening 120; wherein, the screw rod 100 is generally provided with external threads so as to install the screw into the bone for treatment; and the screw rod 100 may be a cylindrical structure with two open ends, a structure with through holes on the side wall, or a cylindrical structure with a plurality of through holes on the side wall. In order to release intraosseous pressure, a plurality of uniformly distributed through holes are generally arranged on the side wall of the screw rod 100, and each through hole is respectively communicated with the central cavity 110. The screw cap 200 generally comprises a cap cover and a flange arranged at a lower end of the cap cover, and is installed by means of a flange, which is generally of a regular hexagonal structure to facilitate the installation of the screw cap 200. After the screw rod 100 is implanted into the bone, the screw cap 200 is used for sealing the exposed end of the screw rod 100. In this way, the central cavity 110 inside the screw rod 100 may not be blocked by food while the patient under treatment is eating. The screw cap 200 is provided with a pressure release part, which facilitates smooth intraosseous pressure release and ensures therapeutic effect. The screw cap 200 can be rotatably arranged on one end of the screw rod 100 by various means, such as a threaded connection, clearance fit or bearing connection and so forth. In the case of intraosseous cleaning, the screw cap 200 is rotated to a position in which the rinsing opening 120 is in communication with the lockable opening 210; that is, a rinsing solution may be added to the central cavity 110 via the rinsing opening 120, thus improving the therapeutic effect on the patient.

Figure 3:
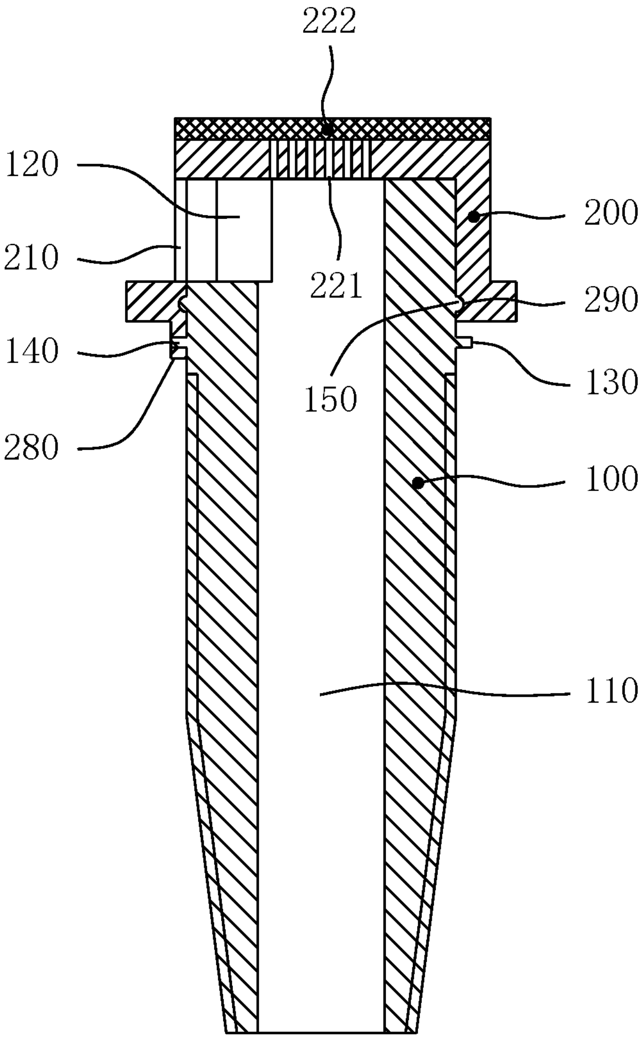
FIG. 3 is a schematic diagram of a second embodiment of the invention.

A fixing structure is arranged on the intraosseous pressure release screw to avoid accidental rotation of the screw cap 200 after the intraosseous pressure release screw is implanted into the patient's bone, and accidental rotation of the screw cap 200 during intraosseous cleaning. The fixing structure includes two states of fixing the screw cap 200; one is the fixing state when the rinsing opening 120 is in communication with the lockable opening 210, and the other is the fixing state when the rinsing opening 120 is not in communication with the lockable opening 210. The above fixing structure can be implemented in various ways, preferably the structures shown in FIG. 3 to FIG. 12, i.e., the lower end of the screw cap 200 is provided with a first clasp 270 and a second clasp 280, the side wall of the screw rod 100 is provided with a first rod head 130 and a second rod head 140 respectively corresponding to the first clasp 270 and the second clasp 280, the first rod head 130 is matched with the first clasp 270 and can be embedded thereinto, and the second rod head 140 is matched with the second clasp 280 and can be embedded thereinto. When the screw cap 200 is rotated until the first rod head 130 is embedded into the first clasp 270, the lockable opening 210 is not in communication with the rinsing opening 120, as shown in FIG. 6 to FIG. 10. When the screw cap 200 is rotated until the second rod head 140 is embedded into the second clasp 280, the lockable opening 210 is in communication with the rinsing opening 120, as shown in FIG. 3. Generally, the radian between the first clasp 270 and the second clasp 280 is smaller than that between the first rod head 130 and the second rod head 140 based on the axis of the screw rod 100.

Figure 4:
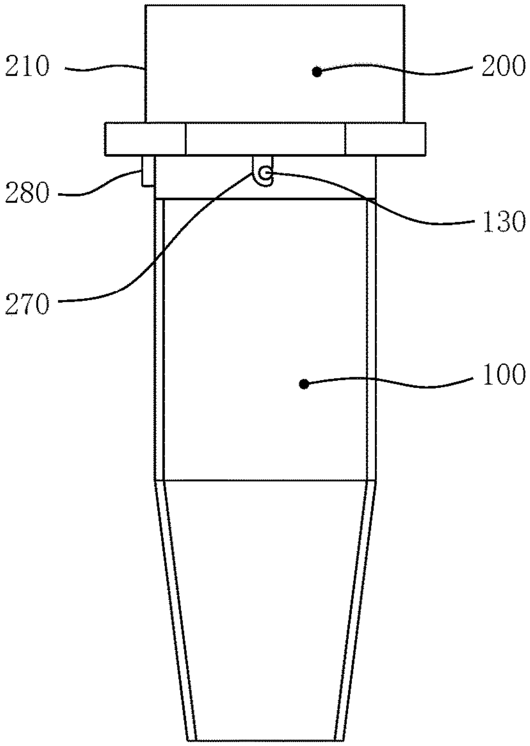
FIG. 4 is a structural diagram of the first rod head embedded into the first clasp according to the second embodiment of the invention.
Figure 5:
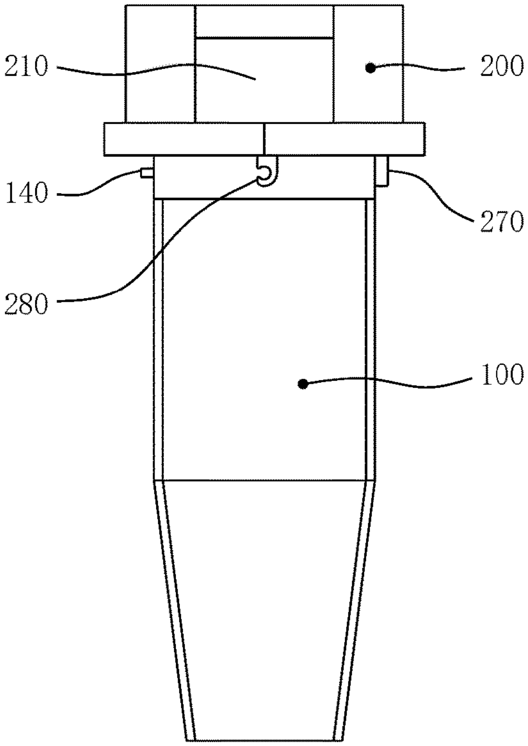
FIG. 5 is a left view of FIG. 4.

Specifically, as shown in FIG. 4 and FIG. 5, the first clasp 270 is provided with an embedding part that can be embedded into the first rod head 130, and the first clasp 270 is also provided with an entrance gap that communicates with the embedding part at the side opposite to the first rod head 130. When the screw cap 200 is rotated to move the first clasp 270 towards the first rod head 130, the first rod head 130 can be embedded into the embedding part on the first clasp 270 through the entrance gap.

Similarly, the second clasp 280 is provided with an embedding part which can be embedded into the second rod head 140, and the second clasp 280 is also provided with an entrance gap that communicates with the embedding part at the side opposite to the second rod head 140. When the screw cap 200 is rotated to move the second clasp 280 towards the second rod head 140, the second rod head 140 can be embedded into the embedding part on the second clasp 280 through the entrance gap.

Wherein, the entrance gaps on the first clasp 270 and the second clasp 280 are located on the side far away from each other, and both the first clasp 270 and the second clasp 280 are made of materials with strong elastic deformation capability, such as rubber.

Preferably, as shown in FIG. 3 and FIG. 6 to FIG. 12, an annular convex structure 150 is arranged on the external side wall of the screw rod 100 disposed on the upper side of the first rod head 130 and the second rod head 140, and a concave structure 290 matching with the convex structure 150 is arranged on the inner wall of the screw cap 200; and the convex structure 150 is embedded into the concave structure 290 so that the screw rod 100 and the screw cap 200 are connected together and can rotate relatively. The above rotatable connection structure can provide convenient assembly/disassembly of the screw rod 100 and the screw cap 200.

Figure 2:
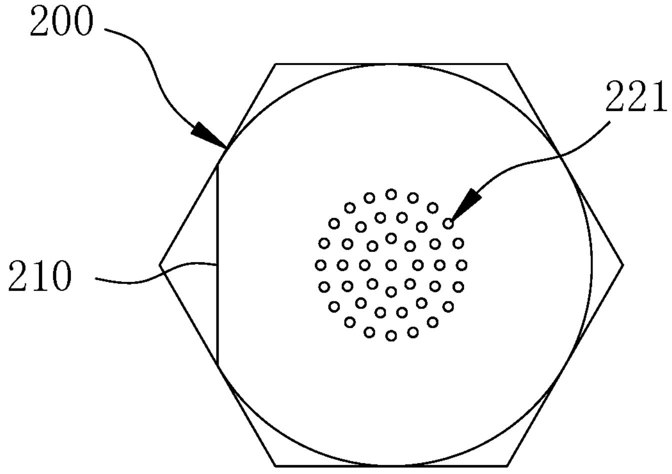
FIG. 2 is a top view of FIG. 1.

Specifically, as shown in FIG. 1, the pressure release part comprises pressure release holes 221 arranged on the screw cap 200. In order to release pressure conveniently, the pressure release holes 221 are usually arranged on the top of the screw cap 200, and the two ends of the pressure release holes 221 are respectively arranged on the inner and outer surfaces at the top of the screw cap 200. Generally, a plurality of pressure release holes 221 are provided and distributed over the screw cap 200 by various means, preferably the distribution mode as shown in FIG. 2, i.e., the plurality of pressure release holes 221 are uniformly distributed directly above the central cavity 110.

In order to prevent fine particles from entering the central cavity 110 of the screw rod 100 via the pressure release holes 221, as shown in FIG. 3, the pressure release part further comprises a filter layer 222 disposed on the outer surface at the top of the screw cap 200, which can be made of filter cloth, dense microporous material, and the like.

Figure 6:
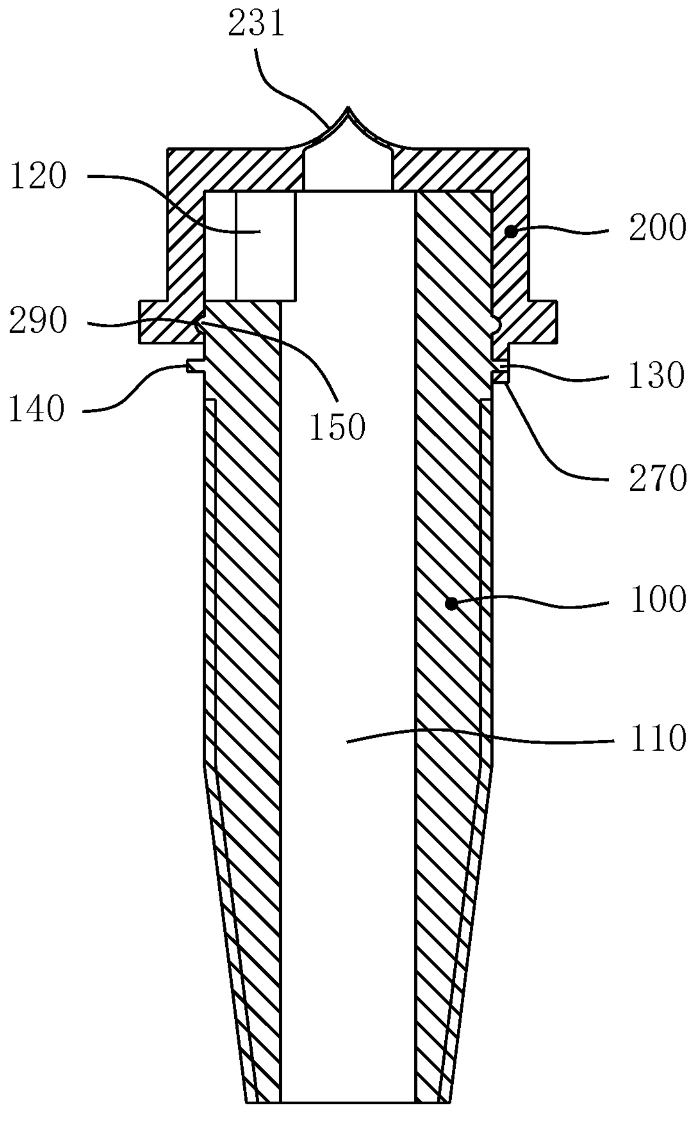
FIG. 6 is a schematic diagram of a third embodiment of the invention.

As a preferred scheme of the invention, as shown in FIG. 6, a pressure release part is provided at the top of the screw cap 200, and comprises at least two concave arc-shaped flaps 231 with the upper ends mutually attached. When the pressure in the central cavity 110 is greater than the atmospheric pressure, the joint of the concave arc-shaped flaps 231 is opened to release the intraosseous pressure. When the pressure in the central cavity 110 is less than or equal to the atmospheric pressure, the concave arc-shaped flaps 231 are in a state of being attached to each other to form a backflow prevention structure similar to a venous flap, which can avoid food entering and divert liquid from entering the central cavity 110.

Figure 7:
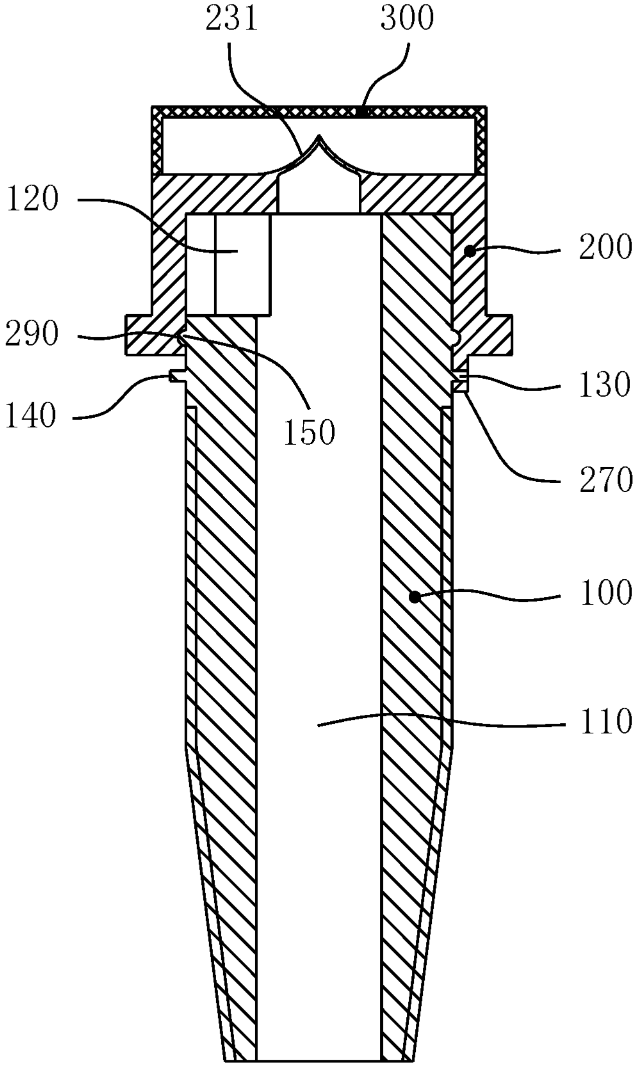
FIG. 7 is a schematic diagram of a fourth embodiment of the invention.

In order to protect the concave arc-shaped flaps 231 and the oral cavity of the patient, as shown in FIG. 7, the intraosseous pressure release screw further comprises a protective guard 300 arranged on the top of the screw cap 200. The protective guard 300 is used to cover the pressure release part formed by the concave arc-shaped flaps 231, and is usually made of mesh material.

Figure 8:
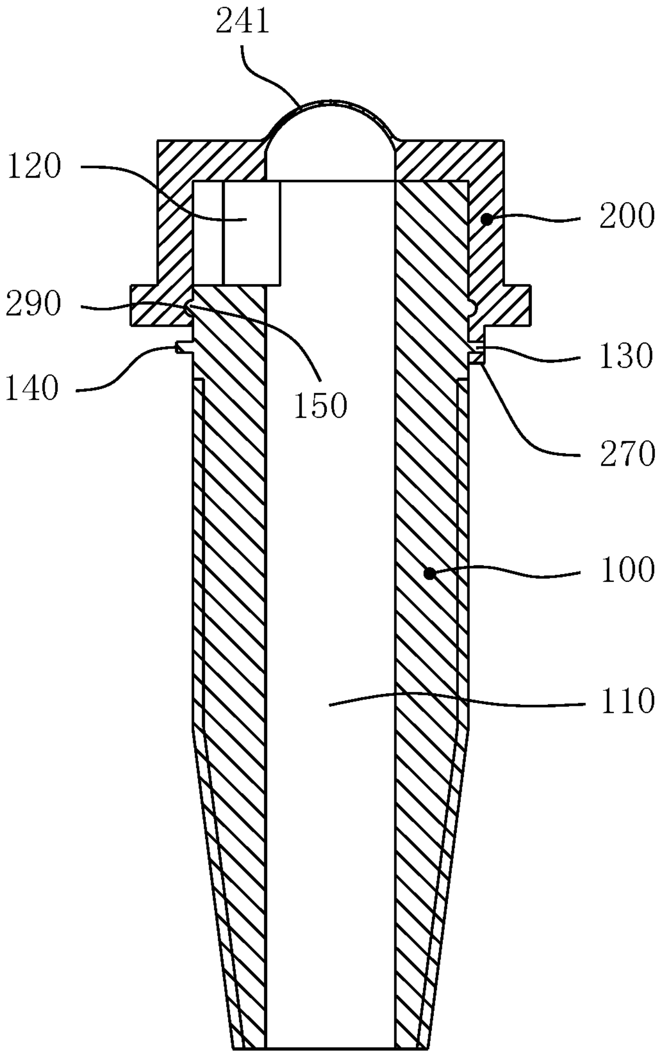
FIG. 8 is a schematic diagram of a fifth embodiment of the invention.

As another preferred scheme of the invention, as shown in FIG. 8, a pressure release part arranged on the top of the screw cap 200 is a spherical arc surface closed end comprising at least three convex arc-shaped flaps 241. When the pressure in the central cavity 110 is greater than the atmospheric pressure, the convex arc-shaped flaps 241 forming a spherical arc surface closed end are opened to release the intraosseous pressure. When the pressure in the central cavity 110 is less than or equal to the atmospheric pressure, the closed end of the spherical arc surface is in a closed state, which can avoid food entering and divert liquid from entering the central cavity 110. Usually, a protective guard 300 is also arranged on the outer cover of pressure release part having the spherical arc closed end structure.

Figure 9:
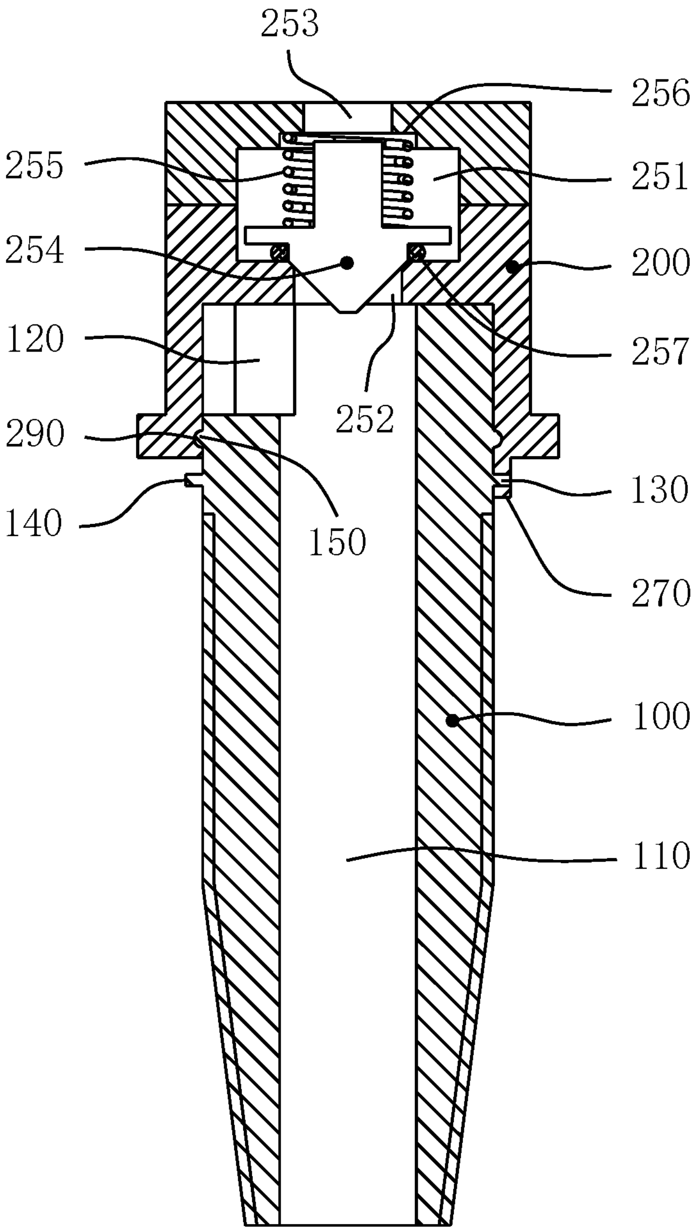
FIG. 9 is a schematic diagram of a sixth embodiment of the invention.

As another preferred scheme of the invention, as shown in FIG. 9, the pressure release part is arranged at the top of the screw cap 200, and comprises a valve cavity 251 with a lower air inlet end 252 and an upper air outlet end 253, a valve core 254 and a spring 255 sequentially arranged in the valve cavity 251 along the air flow direction. A spring slot 256 is arranged at the top wall of the valve cavity 251, with one end of the spring 255 pressing against the valve core 254, and the other end of the spring 255 pressing against the spring slot 256.

Wherein, the top of the screw cap 200 is mainly composed of an upper part and a lower part, which are fixedly connected together by ultrasonic welding and the like after other parts are installed in the valve cavity 251. A valve cavity 251 is arranged in the top of the screw cap 200. The upper part of the valve cavity 251 is an upper air outlet end 253 in communication with the outside, and the lower part of the valve cavity 251 is a lower air inlet end 252 in communication with the central cavity 110. The valve core 254 is generally made of plastics, preferably PP plastics. Normally, the spring 255 presses against the valve core 254 so that the valve core 254 contacts the bottom wall surface enclosing the valve cavity 251 to form a seal. When the pressure in the central cavity 110 is less than or equal to the atmospheric pressure, the valve core 254 contacts the bottom wall surface enclosing the valve cavity 251 to prevent food entering the central cavity 110. When the pressure in the central cavity 110 is greater than the atmospheric pressure, the pressure received by the valve core 254 is greater than the elastic force of the spring 255, and the valve core 254 recedes to open the lower air inlet end 252 and release the pressure in the central cavity 110. The direction of airflow refers to the direction of the airflow when the pressure in the central cavity 110 is discharged from the pressure release part, i.e., the direction from the lower air inlet end 252 to the upper air outlet end 253.

Specifically, as shown in FIG. 9, the valve core 254 comprises a valve core rod and a tapered plug arranged at the end of the valve core rod, and the spring 255 is coiled around the valve core rod and located between the tapered plug and the spring slot 256. The pressure release part also comprises an O-shaped sealing ring 257. The tapered plug is sequentially provided with a conical sealing surface, a cylindrical surface and an annular platform surface along the air flow direction; and the O-shaped sealing ring 257 is arranged between the cylindrical surface and the annular platform surface. A conical surface matching with the conical sealing surface is generally arranged on the bottom wall surface enclosing the valve cavity 251, and the valve core 254 is in contact with the bottom wall surface enclosing the valve cavity 251 to form a surface seal under the action of the spring 255. Under the action of the elastic force of the spring 255, the O-shaped sealing ring 257 and the bottom wall enclosing the valve cavity 251 form a secondary seal, further improving the sealing effect.

Figure 10:
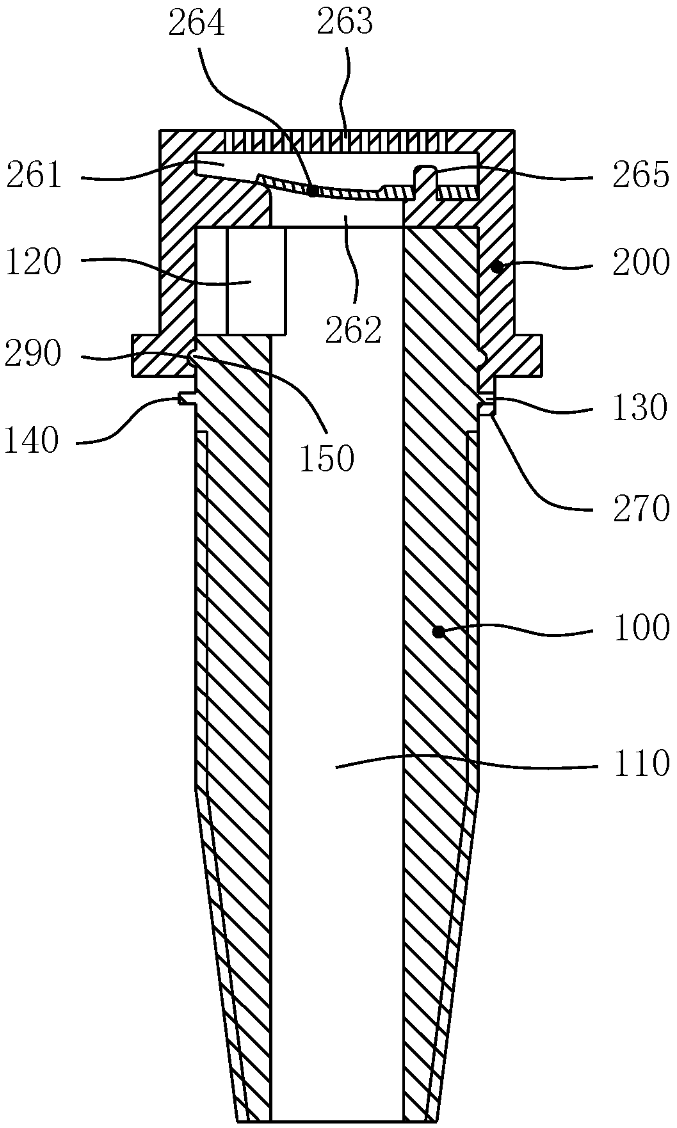
FIG. 10 is a schematic diagram of a seventh embodiment of the invention.
Figure 11:
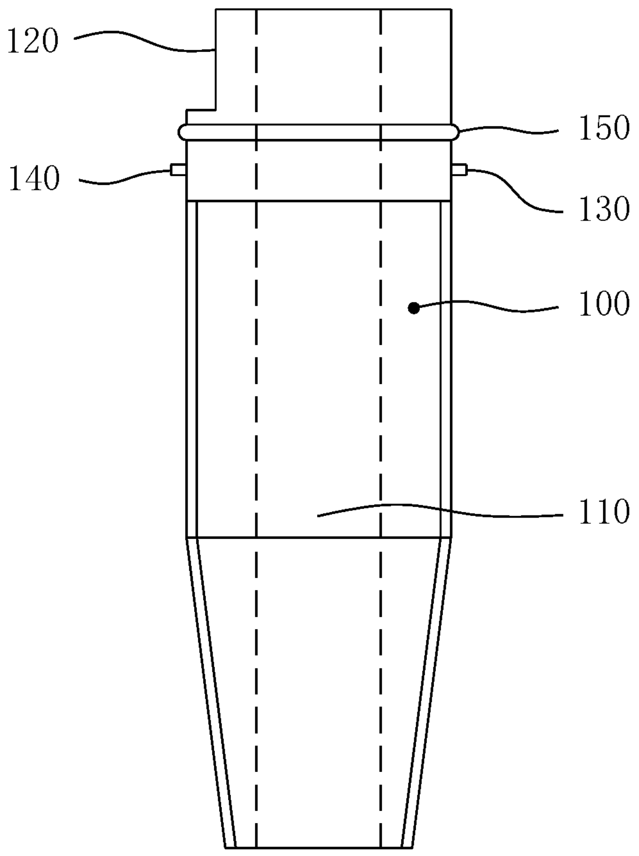
FIG. 11 is a structural diagram of the screw rod according to the second to seventh embodiments of the invention.
Figure 12:
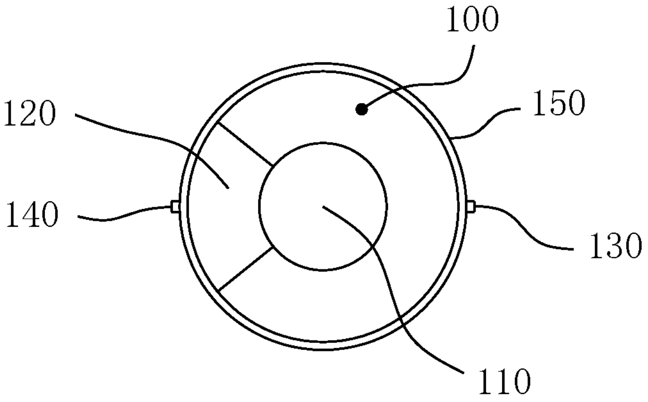
FIG. 12 is a top view of FIG. 11.

As another preferred scheme of the invention, as shown in FIG. 10, the pressure release part is arranged on the top of the screw cap 200, and comprises a cavity 261 with a lower air inlet 262 and an upper air outlet 263, and an elastic valve plate 264 arranged in the cavity 261 and closing the lower air inlet 262. When the pressure in the central cavity 110 is greater than the atmospheric pressure, the free end of the elastic valve plate 264 can move towards the upper air outlet 263 to open the lower air inlet 262.

Wherein, the upper part of the cavity 261 is the upper air outlet 263 in communication with the outside, and the lower part of the cavity 261 is the lower air inlet 262 in communication with the central cavity 110. Generally, the upper air outlet 263 is composed of a plurality of uniformly distributed through holes. The elastic valve plate 264 is usually made of elastic materials, preferably silica gel.

Specifically, as shown in FIG. 10, a valve plate fixing column 265 is arranged on the bottom wall of the cavity 261 located at one side of the lower air inlet 262, one end of the elastic valve plate 264 is fixedly arranged on the valve plate fixing column 242, and the other end of the elastic valve plate 241 is attached to the bottom wall of the cavity 261 on the other side of the lower air inlet 262. The other end of the elastic valve plate 241 is the free end of the elastic valve plate 241.

The invention claimed is:

1. An intraosseous pressure release screw, comprising a screw rod with a central cavity disposed therein, and a screw cap rotatably disposed on one end of the screw rod, wherein the screw cap is provided with a pressure release part communicating the central cavity with the outside; a rinsing opening is arranged on the rod section of the screw rod within the screw cap and is in communication with the central cavity; a lockable opening is arranged on the side wall of the screw cap and can rotate with the screw cap to keep communication with the rinsing opening.

2. The intraosseous pressure release screw according to claim 1, wherein the pressure release part comprises pressure release holes arranged on the screw cap.

3. The intraosseous pressure release screw according to claim 2, wherein the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto; when the screw cap is rotated until the first rod head is embedded into the first clasp, the lockable opening is not in communication with the rinsing opening; when the screw cap is rotated until the second rod head is embedded into the second clasp, the lockable opening is in communication with the rinsing opening.

4. The intraosseous pressure release screw according to claim 2, wherein the pressure release holes are arranged on the top of the screw cap, the two ends thereof are respectively located on the inner and outer surfaces of the top of the screw cap, and the pressure release part further comprises a filter layer on the outer surface at the top of the screw cap.

5. The intraosseous pressure release screw according to claim 4, wherein the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto; when the screw cap is rotated until the first rod head is embedded into the first clasp, the lockable opening is not in communication with the rinsing opening; when the screw cap is rotated until the second rod head is embedded into the second clasp, the lockable opening is in communication with the rinsing opening.

6. The intraosseous pressure release screw according to claim 1, wherein the pressure release part is arranged on the top of the screw cap, and comprises at least two concave arc-shaped flaps with the upper ends mutually attached.

7. The intraosseous pressure release screw according to claim 6, wherein the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto; when the screw cap is rotated until the first rod head is embedded into the first clasp, the lockable opening is not in communication with the rinsing opening; when the screw cap is rotated until the second rod head is embedded into the second clasp, the lockable opening is in communication with the rinsing opening.

8. The intraosseous pressure release screw according to claim 1, wherein the pressure release part is arranged on the top of the screw cap and the pressure release part is a spherical arc surface closed end comprising at least three convex arc-shaped flaps.

9. The intraosseous pressure release screw according to claim 8, wherein the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto; when the screw cap is rotated until the first rod head is embedded into the first clasp, the lockable opening is not in communication with the rinsing opening; when the screw cap is rotated until the second rod head is embedded into the second clasp, the lockable opening is in communication with the rinsing opening.

10. The intraosseous pressure release screw according to claim 1, wherein the pressure release part is arranged at the top of the screw cap, and comprises a valve cavity with a lower air inlet end and an upper air outlet end, a valve core and a spring sequentially arranged in the valve cavity along the air flow direction; and the top wall of the valve cavity is provided with a spring slot, with one end of the spring pressing against the valve core, and the other end thereof pressing against the spring slot.

11. The intraosseous pressure release screw according to claim 10, wherein the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto; when the screw cap is rotated until the first rod head is embedded into the first clasp, the lockable opening is not in communication with the rinsing opening; when the screw cap is rotated until the second rod head is embedded into the second clasp, the lockable opening is in communication with the rinsing opening.

12. The intraosseous pressure release screw according to claim 1, wherein the pressure release part is arranged on the top of the screw cap, and comprises a cavity with a lower air inlet and an upper air outlet, and an elastic valve plate arranged in the cavity and closing the lower air inlet; when the pressure in the central cavity is greater than the atmospheric pressure, the free end of the elastic valve plate can move towards the upper air outlet to open the lower air inlet.

13. The intraosseous pressure release screw according to claim 12, wherein the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto; when the screw cap is rotated until the first rod head is embedded into the first clasp, the lockable opening is not in communication with the rinsing opening; when the screw cap is rotated until the second rod head is embedded into the second clasp, the lockable opening is in communication with the rinsing opening.

14. The intraosseous pressure release screw according to claim 12, wherein a valve plate fixing column is arranged on the bottom wall of the cavity located at one side of the lower air inlet, one end of the elastic valve plate is fixedly arranged on the valve plate fixing column, and the other end thereof is attached to the bottom wall of the cavity on the other side of the lower air inlet.

15. The intraosseous pressure release screw according to claim 14, wherein the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto; when the screw cap is rotated until the first rod head is embedded into the first clasp, the lockable opening is not in communication with the rinsing opening; when the screw cap is rotated until the second rod head is embedded into the second clasp, the lockable opening is in communication with the rinsing opening.

16. The intraosseous pressure release screw according to claim 1, wherein the lower end of the screw cap is provided with a first clasp and a second clasp, the side wall of the screw rod is provided with a first rod head and a second rod head respectively corresponding to the first clasp and the second clasp, the first rod head is matched with the first clasp and can be embedded thereinto, and the second rod head is matched with the second clasp and can be embedded thereinto; when the screw cap is rotated until the first rod head is embedded into the first clasp, the lockable opening is not in communication with the rinsing opening; when the screw cap is rotated until the second rod head is embedded into the second clasp, the lockable opening is in communication with the rinsing opening.

17. The intraosseous pressure release screw according to claim 16, wherein an annular convex structure is arranged on the external side wall of the screw rod located on the upper side of the first rod head and the second rod head, and a concave structure-matching with the convex structure is arranged on the inner wall of the screw cap; and the convex structure is embedded into the concave structure so that the screw rod and the screw cap are connected together and can rotate relatively.

* * * * *